(12) United States Patent
D'Andrea et al.

(10) Patent No.: US 12,326,276 B2
(45) Date of Patent: Jun. 10, 2025

(54) AIR PURIFIER

(71) Applicant: LABORATORI FABRICI SRL, Pordenone (IT)

(72) Inventors: Alessio D'Andrea, San Giorgio Della Richinvelda (IT); Pietro Paolo Felice Ganis, Camino Al Tagliamento (IT); Vincenzo Vitiello, Toscolano-Maderno (IT)

(73) Assignee: LABORATORI FABRICI SRL, Pordenone (IT)

( * ) Notice: Subject to any disclaimer, the term of this patent is extended or adjusted under 35 U.S.C. 154(b) by 921 days.

(21) Appl. No.: 17/427,441

(22) PCT Filed: Jan. 31, 2020

(86) PCT No.: PCT/IB2020/050780
§ 371 (c)(1),
(2) Date: Jul. 30, 2021

(87) PCT Pub. No.: WO2020/157713
PCT Pub. Date: Aug. 6, 2020

(65) Prior Publication Data
US 2022/0099319 A1    Mar. 31, 2022

(30) Foreign Application Priority Data
Feb. 1, 2019 (IT) .................. 102019000001455

(51) Int. Cl.
*A61L 9/00*    (2006.01)
*A01G 9/02*    (2018.01)
(Continued)

(52) U.S. Cl.
CPC ............... *F24F 8/175* (2021.01); *A01G 9/02* (2013.01); *A61L 9/205* (2013.01); *F24F 8/167* (2021.01);
(Continued)

(58) Field of Classification Search
CPC .... F24F 8/167; F24F 8/175; F24F 8/22; F24F 2110/50; A61L 2209/111; A61L 2209/14; A61L 9/205; A01G 9/02
(Continued)

(56) References Cited

U.S. PATENT DOCUMENTS 5,397,382 A * 3/1995 Anderson ............... A01G 9/02
                                                         47/65.5
5,934,017 A    8/1999 Ho
(Continued)

FOREIGN PATENT DOCUMENTS

CN       1486411 A    3/2004
CN     102215940 A   10/2011
(Continued)

OTHER PUBLICATIONS

Chinese Office Action for Chinese Application No. 202080012076.X, dated Apr. 27, 2022, with English translation of Chinese Office Action and Search Report.

*Primary Examiner* — T. Bennett McKenzie
(74) *Attorney, Agent, or Firm* — Birch, Stewart, Kolasch & Birch, LLP

(57) ABSTRACT

An air purifier includes a first pot; a second pot and a fan suitable for creating an air flow between the inside and outside of the air purifier. The second pot which is provided with a bottom and is housed inside the first pot in which the lateral walls of the second pot are formed by a plurality of ribs which extend in the vertical direction of the pot and in which adjacent ribs are arranged essentially parallel to each other, creating slots between them essentially of the length of the ribs. A gap is formed between the first pot and the second pot which extends preferably along the entire length of said slots. The use of the air purifier is also disclosed.

13 Claims, 3 Drawing Sheets

(51) Int. Cl.
*A61L 9/20* (2006.01)
*F24F 8/167* (2021.01)
*F24F 8/175* (2021.01)
*F24F 8/22* (2021.01)
*F24F 110/50* (2018.01)

(52) U.S. Cl.
CPC ........... *F24F 8/22* (2021.01); *A61L 2209/111* (2013.01); *A61L 2209/14* (2013.01); *F24F 2110/50* (2018.01)

(58) Field of Classification Search
USPC .......................................................... 96/224
See application file for complete search history.

(56) References Cited

U.S. PATENT DOCUMENTS

| | | | |
|---|---|---|---|
| 10,596,294 | B2 | 3/2020 | Kim et al. |
| 2002/0104436 | A1 | 8/2002 | Logstrup |
| 2003/0217507 | A1* | 11/2003 | Wolverton ............. A47G 7/041 47/39 |
| 2011/0154985 | A1 | 6/2011 | Mittelmark |
| 2014/0138305 | A1* | 5/2014 | Crandall ............... B24B 37/245 442/411 |
| 2015/0359922 | A1* | 12/2015 | Kim .......................... A61L 9/20 422/121 |
| 2017/0065921 | A1* | 3/2017 | Lo ....................... B01D 46/0005 |
| 2017/0246486 | A1* | 8/2017 | Cazier .................... A61B 5/087 |

FOREIGN PATENT DOCUMENTS

| | | | | |
|---|---|---|---|---|
| CN | 106678976 A | * | 5/2017 | ................ F24F 1/00 |
| CN | 106999845 A | | 8/2017 | |
| DE | 94 03 154 U1 | | 9/1994 | |
| DE | 196 00 008 A1 | | 10/1998 | |
| WO | WO2018/133193 A1 | | 7/2018 | |
| WO | WO2018/211307 A1 | | 11/2018 | |

* cited by examiner

AIR PURIFIER

TECHNICAL FIELD

The present invention relates to an air purifier in which the air purification takes place through a plant and the culture matrix thereof in a natural way. A ventilation system optimizes the air filtration through plant and matrix. In this regard, the air purifier comprises a first pot and a second pot which is housed inside the first pot and a fan.

STATE OF THE ART

To make the atmosphere into living or working spaces healthy, the market has developed various types of air purification devices. In general, air purifiers are devices that eliminate contaminants, toxic agents, powders, VOCs (Volatile Organic Compounds), etc. from the air through filters of different types. A natural air purifier is a device that uses the roots of plants or also the matrix in which they grow as filters.

In the roots there are microorganisms that actively biofiltrate toxic agents and decompose them. Currently available natural air purifiers promote the transport of air to the roots and/or culture matrix with ventilation systems integrated in the pots, as described, e.g., in US documents US 2015/0282436 A1, U.S. Pat. No. 6,230,437 B1 and US 2011/0154985 A1. In these systems the air flow is not optimized within the pot which contains the plant and the matrix, as well as the purification itself which is not fully satisfying yet.

DISCLOSURE OF THE INVENTION

The object of the invention is to propose an improved air purifier for purifying the air in internal spaces, in particular an air purifier with an optimized air flow to the roots and through the matrix in which the roots are rooted. Another object of the invention is to further improve the degree of air purification with respect to the state of the art. These objects and others which will become evident from the following description of the invention are obtained by an air purifier as defined in the first claim, and precisely by an air purifier which comprises:

(a) a first pot;
(b) a second pot which is provided with a bottom and is housed inside the first pot in which the lateral walls of the second pot are formed by a plurality of ribs which extend in the axial direction of the pot and in which adjacent ribs are arranged essentially parallel to each other, creating slots between them essentially of the length of the ribs, wherein a gap is formed between the first pot and the second pot which extends preferably at least along the entire length of said slots; and
(c) a fan suitable for carrying out an air flow between the inside and the outside of said air purifier.

The insertion of the second pot with the ribs in the first pot creates said gap between the walls of the pots and admit a defined air flow which is channeled through the slots also linearly towards the bottom of the system. Then, the slots allow the roots to exit from the second pot and their "diffusion" in the gap, where air enters easily to reach the roots.

The axial direction of the pot is to be understood as the vertical direction to the support surface, where the pot is placed.

In an advantageous variant of the invention, the fan is placed horizontally under the bottom of the second pot. Such a position creates a vertical air flow inside the purifier.

In a preferred variant of the invention, the bottom of the second pot is located at a certain height inside the lateral walls of the second pot and the ribs are arranged around the bottom extending beyond the bottom downwards and optionally also forming at least a part of the bottom admitting an air flow along the slots from the part of the second pot which is located above the bottom towards the part of the second pot which is located below the bottom and creating a space under the bottom inside the lateral walls. To form a part of the bottom, the ribs branch off at the height of the bottom to continue downwards in a linear shape and in a curved shape inside the bottom.

Particularly preferred is a variant of the invention, wherein the air purifier further comprises (d) an air permeable photocatalytic filter arranged between the bottom of the second pot and the fan and (e) a light source for activating the catalyst of the photocatalytic filter. The addition of the photocatalyst adds a further contribution to the purification, being the filter capable of degrading other compounds with respect to the natural components of the system. Preferably, the filter is arranged in the space created under the bottom inside the lateral walls of the second pot.

Advantageously, the purifier according to the invention contains sensors to measure the air quality and a control and communication unit to manage the sensors, indicate the air quality and manage the fan speed based on the values detected by the sensors. These components are suitable for making the system autonomous and automatic.

Preferably, the first pot comprises a bottom which is provided with
(i) a tubular part which protrudes towards the inside of the pot and which comprises a grid under which the fan can be positioned inside this tubular part; and
(ii) a case for the sensors and the control and communication unit.

In a further embodiment of the invention, the purifier according to the invention with tubular part and case preferably further comprises
(iii) a water tank placed on the bottom of the first pot and surrounding the tubular part and the case; and
(iv) channels created in the bottom of the second pot which lead directly to the tank.

The water tank can be used for automatic irrigation of the system (if provided with relative ropes or capillaries that connect inside the second pot and/or the gap to supply water to the roots) and/or for the collection of water in excess. The presence of channels helps to channel the water flows.

The case is advantageously a recess in the external pot of the air purifier which is closed by an interface which communicates information on the system status to the user; i.e. preferably the case and the wall of the first pot each have an opening placed in correspondence between them to position LEDs and an interface for communicating with the user and possibly a light diffuser.

Advantageously, the lid is provided with a series of oblique cuts that allow outside air to enter the sensor chamber for analysing the air quality. The cuts have been designed advantageously with a grating system to protect the electronic part from any water coming from the outside but guarantee a correct air flow.

In a very preferred variant of the invention, in the gap there is a granular matrix, in particular expanded clay, preferably with a grain size equal to or greater than 8 mm, more preferably with a grain size in the range from 8 to 16 mm determined according to the UNI EN 13055-2 standard, paragraph 4.3. This granular matrix has deflector capacities, like the ribs of the second pot, and can be penetrated by roots through the interstices. These characteristics allow a good passage of air and a good accessibility to the roots that are also found in the channels (interstices) created between the granules that act as deflectors.

The purification system illustrated is characterized by two stages, the first entirely natural consists of the plant and its root apparatus, the second consists of a photocatalytic filter, in particular a ceramic honeycomb filter ($SiO_2$) treated with titanium dioxide ($TiO_2$) and activated with UVA type ultraviolet LED light.

One of the active hearts of the purification system is the plant. In nature, plants have the ability to remove harmful agents present in the air not only through their volatile part (the leaves) but also through the root apparatus and its interaction with the cultivation substrate. In this lower region of the plant, bio-chemical processes take place which permit to block and degrade/convert harmful substances present in the external air, purifying the air.

The system according to the invention has been designed to amplify and make this natural property of common houseplants more effective.

To ensure a greater and constant air flow through the root apparatus, the upper part of the air purifier has been designed by carefully calibrating the full and empty areas.

The key element is the central crown, that is the second ribbed pot, where the plant is housed. The crown is characterized by a series of ribs arranged at regular intervals, which keep the plant in an optimal position, leaving the space necessary for the passage of the air flow and the growth of the roots.

Between the central crown and the internal wall of the pot, a gap is created, which is advantageously filled with inert material (for example expanded clay) and has the function of regulating the supply of air between the first filtering stage (the plant) and the second (the photocatalytic filter), balancing it and significantly increasing the air flow.

With this system, the growing roots of the plant will invade the gap, thus ensuring better growth for the plant and an increase in purification capacity.

In the studies conducted by the inventors, it has been noted that this first filtering stage is particularly effective in the abatement of VOCs (volatile organic compounds).

In the second stage, the air purifier houses a photocatalytic filter, consisting for example of a ceramic honeycomb filter, 140 mm in diameter, dip-coated with titanium dioxide ($TiO_2$) nanoparticles, and activated by four UVA LEDs. Other filters that the person skilled in the art can easily identify with his general knowledge are conceivable.

Photocatalysis is a natural process by which light hits a mineral (such as titanium dioxide—$TiO_2$—a common mineral) and activates a chemical process that safely and instantaneously oxidises and decomposes organic matter to form water steam and carbon dioxide.

All the air conveyed by the ventilation system ultimately passes through this second filtering stage, which guarantees the elimination of viruses, bacteria and odours.

Such a filter is not subject to wear, it does not need to be replaced, but it's necessary to simply wash it with running water to clean it.

The combination of photocatalysis with the plant guarantees a significant improvement in purification performance.

The air purifier according to the invention, thanks to a forced air ventilation system (preferably characterized by a fan placed horizontally), advantageously completely automated, conveys the external air inside the filtering system, first towards the root apparatus of the plant, then towards the photocatalytic filter, to then come out of the system, for example from an opening located along the lower edge of the pot.

The slots in the crown have the following functions:
Avoid spilling of the soil as much as possible;
allow the roots to grow and "invade" the gap filled with the granular material; increasing the purification capacity;
adequately contain the plant;
increase the air passage, much more than the perforated pot, for example, described in document WO/2018/211307 in the name of the applicant, therefore in addition to the above benefits, there is the main advantage of the greater air passage and a high air supply to the photocatalytic filter;
allow the root part to be much more exposed to the air, the interaction of these exposed parts with the air conveyed inside thanks to the natural air deflectors (see the gap with granular material) increases the filtering capacity of the plant; and
increase the air flow through the gap which allows to balance the air rate inside the system. With the deflectors in the shape of a granular material, the air is channeled, which balances the air permeability of the soil. In this way, a system is created which has an air supply evenly distributed between the plant and the photocatalytic filter.

A further aspect of the invention relates to a use of the air purifier according to the invention, containing a plant in the second pot, to purify the air of a space
(I) activating said fan,
(II) passing the air through the gap and said second pot by the activity of said fan;
(III) conveying the air after said passages along said slots towards said fan passing first, if present, through said photocatalytic filter; and
(IV) discharging the air purified by the roots of the plant contained in the second pot, by matrices where present contained in the second pot and in the gap and by the photocatalytic filter, if present, outwards, and optionally
(V) managing the air flow by adjusting the fan speed according to the values measured by the air quality sensors.

The features described for one aspect of the invention may be transferred mutatis mutandis to the other aspect of the invention.

Embodiment variants of the present invention and further objects and advantages are described hereinafter with reference to the drawings. Embodiment variants of the invention are the object of the dependent claims. The description of preferred executive examples of the air purifier and his use according to the invention is only given in an exemplary and non-limiting manner.

DESCRIPTION OF A PREFERRED EXECUTIVE EXAMPLE

Figure 1:
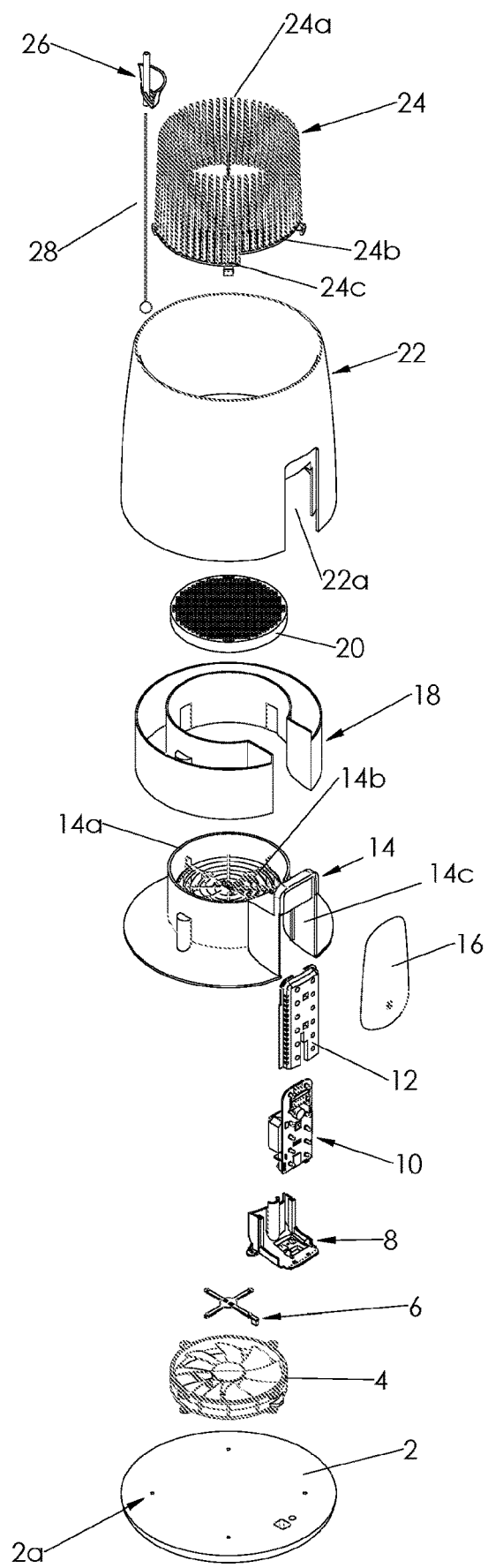
FIG. 1 is an exploded view of a first embodiment variant of an air purifier according to the invention.

FIG. 1 is an exploded view of an embodiment variant of an air purifier according to the invention. Starting from the bottom, there is a base 2 which can be made of various materials, such as metal, plastic or wood, such as beech wood. On the base 2 the entire remaining system is constrained by means of screws to be inserted in the four holes 2a, for example, applied in the base 2. In the lower part, the base 2 has a milling around the perimeter of the same which allows the housing of a power cable (not shown).

On the base 2 there is a fan 4 which is arranged in a horizontal position but causes an air vortex in the axial direction of the air purifier. A 12V fan with a diameter of 140 mm and a height of 25 mm, designed to minimize noise, can be chosen as a fan 4. Its maximum rotation is 1500 rpm (+/−10%). Its maximum flow rate in ideal conditions is 133.7 $m^3$/h; its maximum noise emission is 25.8 dB (A). Thanks to the fan 4, the external air is conveyed into the system, passing through the central crown 24 and the gap 30, as will be illustrated with reference to FIGS. 2b and 3.

Above the fan 4 there is a LED UVA board 6 (light emitting diode of the ultraviolet type A), i.e. an electronic board that houses four UVA LEDs that allow the activation of a photocatalytic filter 20 thanks to their light beam.

An electronic closing box 8 made of ABS (acrylonitrile butadiene styrene) is then provided, which represents the closing system of the entire electronic part by means of two screws.

The electronic board 10 represents the brain of the product, in addition to a LED system, a power connector and a reset button, it houses temperature, humidity, VOC (volatile organic compounds), CO (carbon monoxide), $CO_2$ (carbon dioxide), PM2.5 (particulate material having an average aerodynamic diameter of less than 2.5 μm) and proximity sensors. It also has a connectivity system consisting of: a Wi-Fi module; a Bluetooth module; a microcontroller to remotely manage the system.

A light diffuser 12, made of semitransparent material, is capable of diffusing and amplifying the LED light beam. In addition to its main feature, on both sides it is provided with a series of oblique cuts that allow outside air to enter the sensor chamber for air quality analysis. The cuts have been designed with a grating system to protect the electronic part from any water coming from the outside but guarantee a correct air flow.

A carcass bottom 14, here made of ABS, is the support on which all product technology is mounted. It houses the honeycomb photocatalytic filter 20, the lid 16 for the components 8 and 10 previously illustrated, the UVA LED board 6, the fan 4, and, within a space 14c, the light diffuser 12, the electronic board 10 and the electronic closing box 8.

The lid 16 is made of bioplastic, and represents the product interface. Thanks to a series of LEDs placed on the back, it communicates the air quality to the user through a light code.

On the carcass 14, another annular-shaped carcass is placed which acts as a tank 18 which is made of bioplastic and houses about 1.5 litres of water. The tank 18 surrounds a cylindrical or tubular part 14a of the carcass 14 which comprises a grid 14b which protects from the wings of the fan 4 and serves as a support for the photocatalytic filter 20 admitting at the same time an air flow.

The honeycomb filter 20 is made of ceramic sponge ($SiO_2$), has a diameter of 140 mm and is dip-coated (coating by immersion) with titanium dioxide ($TiO_2$) nanoparticles and is used for photocatalysis.

Everything described so far is housed on the base 2 inside a pot (composed of lateral walls 22 and a bottom 14) which has an opening 22a which can be closed by the lid 16.

The pot also receives a part of the heart of the invention, and precisely a crown 24 which serves as a container for the matrix for the roots of the plant to be grown in the natural air purifier. The crown is also made of bioplastic, it houses the plant and allows a greater air flow into the system. It is characterized by a series of ribs 24a placed at regular intervals creating slots between the ribs 24a. In the shown example, the ribs, i.e. rod-shaped elements, 24a are arranged in a vertical position around a ring 24b spaced from each other to form a slot each time between two adjacent ribs creating a succession of a series of essentially parallel slots which extend around the entire perimeter of the crown 24 and across the entire height thereof. At a certain height inside the crown 24 there is a bottom 15 provided with four drain channels 24c which lead directly to the tank 18, thus allowing excess water present in the lower part of the crown to drain onto the bottom 15 and into the tank 18 without invading the electronic part of the system. The air can pass along the entire length of the slot passing from the part of the crown 24 upper to the bottom 15 to the part of the crown 24 lower to the bottom 15, the ribs 24a being placed perimetrically around the bottom 15 whose perimeter essentially coincides with the ring 24b. The diameter of the crown 24 is greater than that of the cylindrical part 14a of the carcass 14; so that between the two components an opening of about 1 cm is created which allows the water to flow also directly into the tank (this opening is provided for a possible not recommended watering of the plant from above).

A self-watering cap 26 made of semitransparent plastic material and a float 28 housed by the latter complete the system. The float 28 is made of plastic and expanded material and marks the water level in the tank.

Figure 2A:
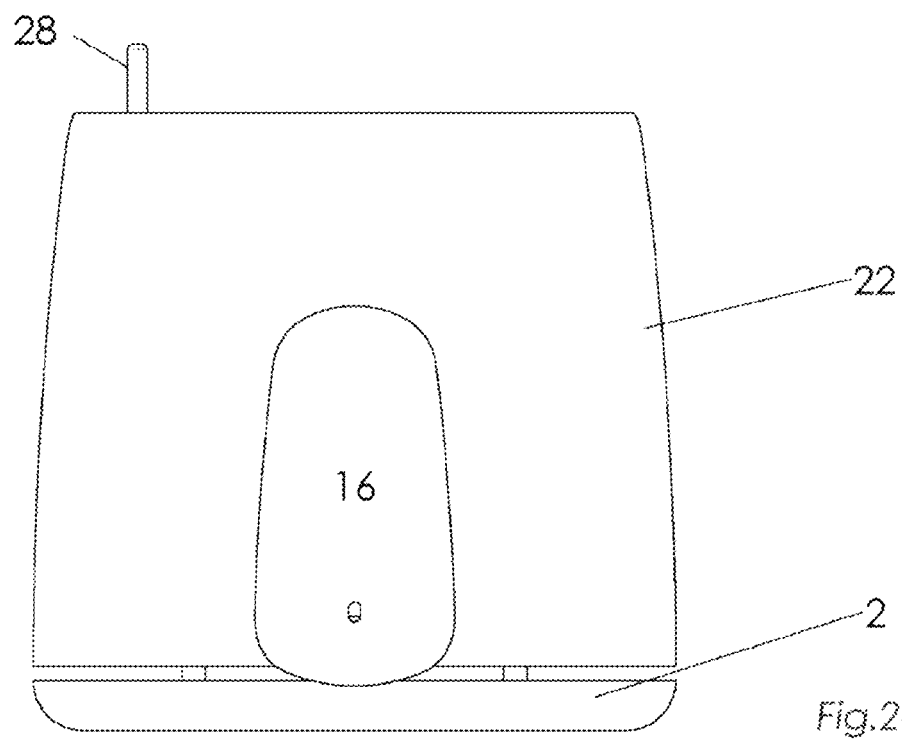
FIG. 2a shows a side view of the air purifier of FIG. 1 in the assembled state.

FIG. 2a shows a side view of the air purifier of FIG. 1 in the assembled state. The pot is applied on the base 2 so as to leave an empty space between both for the passage of the air coming out of the pot. The lid 16 closes the opening 22a (not visible) which contains the electronic boards. Note also the float 28.

Figure 2B:
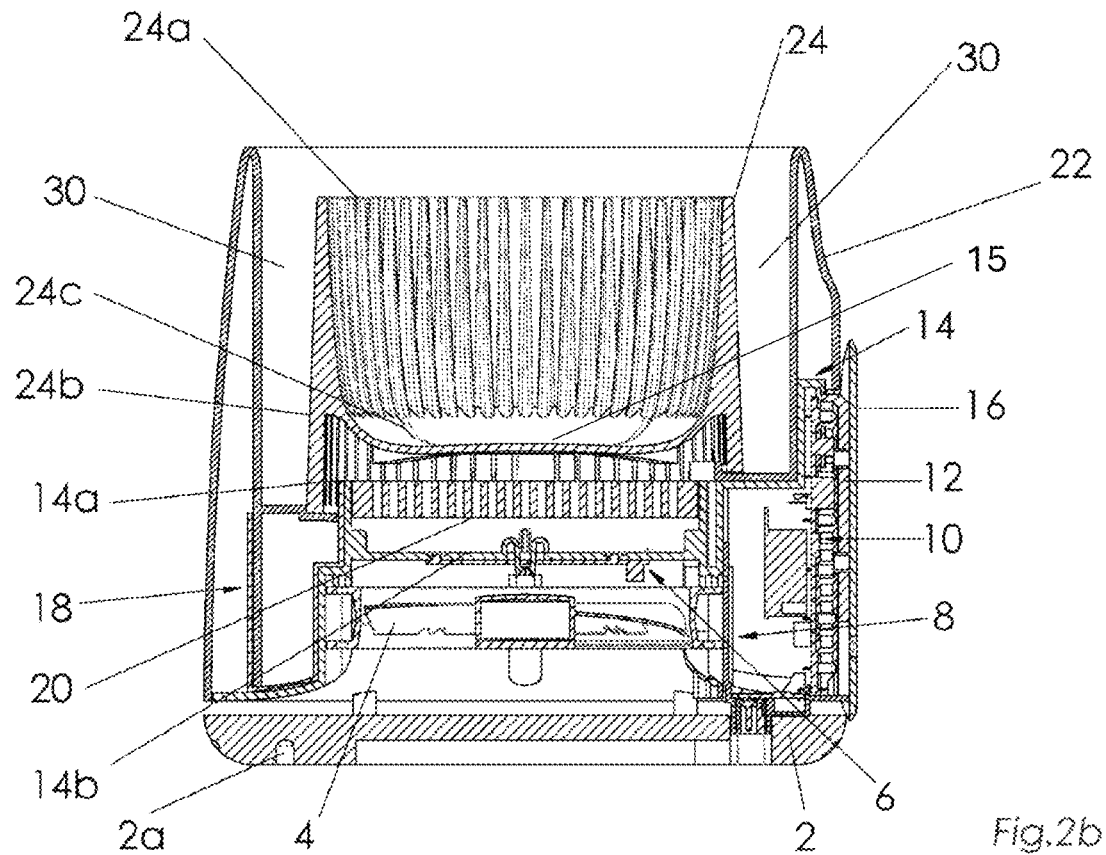
FIG. 2b illustrates the assembled air purifier of FIG. 2a in a section view.

FIG. 2b illustrates the assembled air purifier of FIG. 2a in a section view. The crown 24 and the photocatalytic filter 20 are permeable to air thanks to respective holes in the filter and the passages created by the slots between the ribs 24a in the crown 24. A gap 30 is observed between the inner wall of the pot 22 and the crown 24 which allows to direct an air flow entering the pot from above through this gap 30 and the slots in the crown 24. The air flows created inside the system are evident from FIG. 3.

Figure 3:
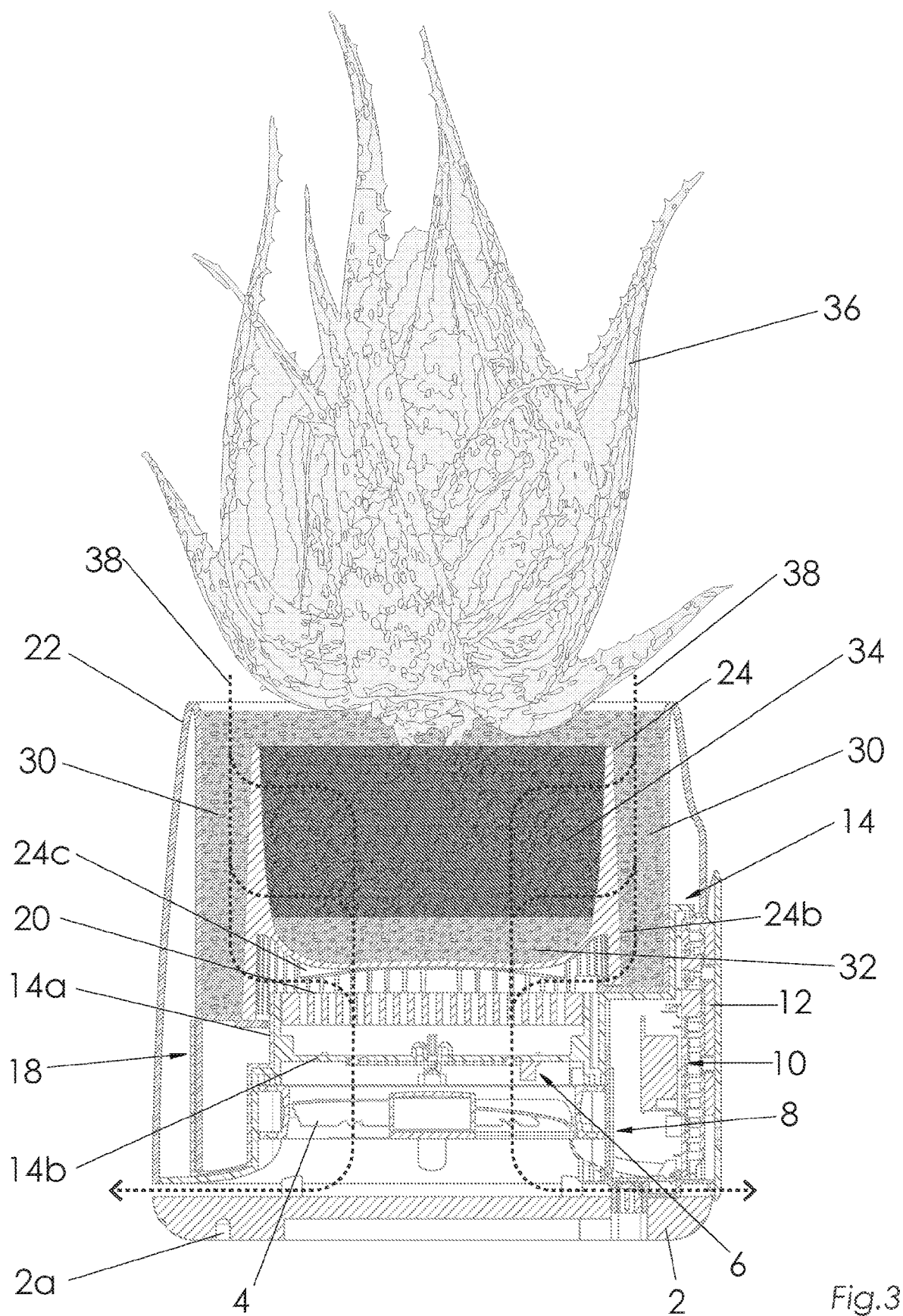
FIG. 3 shows the air purifier in the view of FIG. 2b provided with cultivation matrices and a plant and indicating the air flows inside the purifier.

FIG. 3 shows the air purifier in the view of FIG. 2b provided with cultivation matrices and a plant 36 indicating the air flows 38 inside the purifier. The gap 30 is filled with an inert expanded material which, thanks to the pores created therein, allows an air passage. The crown 24 is filled in the lower part 32 by the same expanded material as the gap 30 and in the upper part 34 by a soil particularly suitable for the purposes, as described, for example, in the patent application of the same applicant IT 102018000002488 with filing date Feb. 8, 2018 not yet published. The soil comprises a mixture of an organic matter containing soil and a granular material of a grain size between 0.5 and 10 mm. Above is a layer of expanded material again. The plant 36 develops roots that also cross the slots in the crown 24 and reach the gap 30. The air passing through the latter easily reaches the roots which provide an efficient natural air purification. Activating the fan 4, the air, following the direction of the arrows 38, enters the gap 30 and the crown 24 passing the relative matrices contained therein and reaches the roots to be conveyed then towards the bottom 15 of the crown 24 and along the slots which it passes through in the part of the crown 24 below the bottom 15 to pass the photocatalytic filter 20 which is activated by the UVA LED board 6, all drawn by the action of the fan 4 below. The air path 38 follows the axial direction of the purifier.

The air purifier presented is a smart pot that combines an innovative natural air purification system, based on the phytodepuration principle, with a sophisticated air monitoring system with sensors, all managed through an application.

The purifier is also provided with a passive self-watering system, consisting of a tank with 1.5 litres capacity, and two cords, which by capillarity allow the plant to absorb the necessary amount of water. In the upper part of the pot there is a cap in semitransparent material, from which you can see the water level by means of a float.

The invention has been presented and described in connection with various embodiment variants. For those skilled in the art and familiar with the subject it is clear that changes and variations that may occur, like materials, sizes, different design shapes are not excluded from the concept of the invention and from the scope of protection as defined by the appended claims.

The invention claimed is:

1. An air purifier comprising:
   (a) a first pot;
   (b) a second pot provided with a bottom and being housed inside the first pot, wherein lateral walls of the second pot are formed by a plurality of ribs extending in an axial direction of the second pot, and wherein adjacent ribs are arranged essentially parallel to each other, creating slots therebetween, the slots being essentially a length of the ribs, and wherein a gap is formed between the first pot and the second pot, the gap extending at least along the entire length of said slots; and
   (c) a fan suitable for carrying out an air flow between an inside and an outside of said air purifier,
   wherein the bottom of the second pot extends in a horizontal direction from an inside surface of the lateral walls of said second pot at a point located above a bottom of the lateral walls in the axial direction,
   wherein the ribs are arranged around said bottom of the second pot extending beyond the bottom of the second pot downwards to admit an air flow along said slots from part of said second pot located above the bottom of the second pot towards part of said second pot located under the bottom of the second pot and creating a space under the bottom of the second pot inside said lateral walls, and the bottom of the second pot forming an upper surface of the space,
   wherein said air purifier further comprises:
   (d) an air permeable photocatalytic filter arranged between the bottom of the second pot and the fan; and
   (e) a light source for activating the catalyst of the photocatalytic filter, and wherein the photocatalytic filter is arranged in the space created under the bottom of the second pot inside the lateral walls of the second pot.

2. The air purifier according to claim 1 wherein said fan is placed horizontally under said bottom of said second pot.

3. The air purifier according to claim 1, further comprising sensors for measuring air quality and a control and communication unit for managing said sensors, indicating the air quality and managing fan speed based on values detected by the sensors.

4. The air purifier according to claim 3 wherein a bottom of said first pot is provided with:
   (i) a tubular part protruding towards the inside of the first pot and including a grid under which said fan can be positioned inside the tubular part, and
   (ii) a case for said sensors and said control and communication unit.

5. The air purifier according to claim 4 further comprising:
   (iii) a water tank placed on said bottom of said first pot and surrounding said tubular part and said case, and
   (iv) channels created in the bottom of said second pot which lead directly to said tank.

6. The air purifier according to claim 4 wherein said case and a wall of said first pot each have an opening placed in correspondence therebetween to place LEDs and an interface.

7. The air purifier according to claim 1, wherein in the gap there is a granular matrix.

8. The air purifier according to claim 7 wherein said granular matrix has a grain size equal to or greater than 8 mm, determined according to the UNI EN 13055-2 standard, paragraph 4.3.

9. The air purifier according to claim 1 wherein the second pot comprises a plant.

10. A method of using the air purifier according to claim 1, containing a plant in the second pot, to purify the air of a space, the method comprising:
    activating said fan;
    passing the air through the gap and said second pot by the activity of said fan (4);
    conveying the air after passing through the gap and the second pot along said slots towards said fan, passing through said photocatalytic filter, and
    discharging the air purified by the roots of the plant contained in the second pot, by matrices, where present, contained in the second pot and in the gap and by the photocatalytic filter outwards, and optionally
    managing the air flow by adjusting the fan speed according to the values measured by air quality sensors.

11. The air purifier according to claim 7, wherein the granular matrix is expanded clay.

12. The air purifier according to claim 7 wherein said granular matrix has a grain size in the range from 8 to 16 mm, determined according to the UNI EN 13055-2 standard, paragraph 4.3.

13. The air purifier according to claim 2, further comprising sensors for measuring air quality and a control and communication unit for managing said sensors, indicating the air quality and managing fan speed based on values detected by the sensors.

\* \* \* \* \*